(12) United States Patent
Lewis et al.

(10) Patent No.: US 6,419,895 B1
(45) Date of Patent: Jul. 16, 2002

(54) CRYSTALLINE ALUMINOSILICATE ZEOLITIC COMPOSITION: UZM-4

(75) Inventors: Gregory J. Lewis; Jaime G. Moscoso, both of Mt. Prospect; Mark A. Miller, Niles; Ben A. Wilson, Algonquin, all of IL (US)

(73) Assignee: UOP LLC, Des Plaines, IL (US)

( * ) Notice: Subject to any disclaimer, the term of this patent is extended or adjusted under 35 U.S.C. 154(b) by 67 days.

(21) Appl. No.: 09/705,653

(22) Filed: Nov. 3, 2000

(51) Int. Cl.$^7$ .............................................. C01B 39/48
(52) U.S. Cl. ....................... 423/718; 423/705; 423/708; 208/46
(58) Field of Search ................................ 423/718, 705, 423/708; 208/46

(56) References Cited

U.S. PATENT DOCUMENTS

| | | | |
|---|---|---|---|
| 2,991,151 A | | 7/1961 | Breck et al. |
| 3,010,789 A | * | 11/1961 | Milton |
| 4,661,332 A | * | 4/1987 | Vaughan et al. |
| 4,698,217 A | * | 10/1987 | Valyocsik |
| 4,826,667 A | * | 5/1989 | Zones et al. |
| 4,891,200 A | * | 1/1990 | Fajula et al. |
| 5,000,932 A | * | 3/1991 | Vaughan |
| 5,248,491 A | * | 9/1993 | Skeels et al. |
| 5,382,420 A | | 1/1995 | Vaughan ...................... 423/716 |

OTHER PUBLICATIONS

"Identification and Charcterization of Zeolites Synthesized in the $K_2O-Al_2O_3-SiO_2-H_2O$ System" by John D. Sherman, Molecular Sieves—II (102) 30, 1974.

"Some Synthetic Potassium Zeolites and Their Properties"by Zhdanov et al., Doklady Chemistry, Proc. Acad. Sci. USSR, 156, 756, 1964.

"Investigation of the Conditions of Crystallization of Zeolites in the System $K_2O-Al2O3-SiO2-H2$) and their Properties", by Ovsepyan et al., Bull. Acad. Sci. USSR., Chemical Science, 1, 8, 1965.

"Chemistry of Soil Minerals." by Barrer et al., J. Chem. Soc. (A) 2475, 1968.

"The Synthesis and Properties of Synthetic Zeolite Linde Q" by Andries et al. Zeolites, 11, 116, 1991.

"The Crystal Structure of Zeolite Linde Q: A proposal based on powder X–ray diffraction and$^{27}$ Al and$^{29}$Si MAS n.m.r spectroscopy" by Andries et al., Zeolites, 11, 124, 1991.

* cited by examiner

*Primary Examiner*—David Sample
(74) *Attorney, Agent, or Firm*—John G. Tolomei; Frank S. Molinaro

(57) ABSTRACT

Applicants have synthesized a new aluminosilicate zeolite identified as UZM-4. This new zeolite has the BPH morphology and is structurally related to zeolite Q. UZM-4 has en empirical formula of

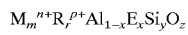

$$M_m^{n+}R_r^{p+}Al_{1-x}E_xSi_yO_z$$

where M is an alkali or alkaline earth metal ion, R can be a quaternary ammonium ion and E can be gallium, iron, boron, chromium, indium and mixtures thereof. The Si/Al ratio can range from 1.5 to about 4.0

16 Claims, No Drawings

CRYSTALLINE ALUMINOSILICATE ZEOLITIC COMPOSITION: UZM-4

FIELD OF THE INVENTION

This invention relates to an aluminosilicate zeolite having the BPH topology and designated UZM-4. The UZM-4 composition is structurally related to zeolite Q, but is thermally stable up to a temperature of 600° C. and has higher Si/Al ratios in the range of about 1.5 to about 4.0.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure.

One particular zeolite, designated zeolite Q, was first disclosed in U.S. Pat. No. 2,991,151. The general formula for zeolite Q is represented in terms of mole ratio of the oxides by the following:

$$0.95 \pm 0.05 \ M_{2/n}O:Al_2O_3:2.2 \pm 0.05 \ SiO_2:xH_2O$$

where M designates at least one exchangeable cation, n represents the valence of M and x has a value from 0 to about 5. The examples in the patent are prepared with M being potassium. Synthesis of zeolite Q was conducted at 25° C. to 50° C. After activation at about 130° C., zeolite Q was found to adsorb small polar molecules.

In a paper by John D. Sherman entitled, "Identification and Characterization of Zeolites Synthesized in the $K_2O$—$Al_2O_3$—$SiO_2$—$H_2O$ System," *Molecular Sieves—II*(102) 30, 1974, he reports that the zeolite Q of the '151 patent is the same zeolite as zeolite K-I reported by other researchers. Zeolite K-I was first reported by S. P. Zhdanov and M. E. Ovsepyon in *Doklady Chemistry. Proc. Acad. Sci. USSR*, 156, 756 (1964). M. E. Ovsepyan and S. P. Zhdanov further reported on K-I zeolite in *Bull. Acad. Sci. USSR, Chem. Sci.* 1, 8 (1965). R. M. Barrer et al. in J. Chem. Soc. (A) 2475 (1968) showed that K-I decomposed at 168° C. It is also reported by Sherman and other researchers that zeolite Q is unstable above 130° C. and is totally disintegrated at 200° C. Owing to this thermal instability, zeolite Q has received little industrial interest. K. J. Andries et al., in *Zeolites*, 11, 124 (1991) proposed the BPH topology for zeolite Q. Synthesis of a pure form of zeolite Q was reported by K.J. Andries et al., in *Zeolites*, 11, 116 (1991). Finally, U.S. Pat. No. 5,382,420 discloses a composition designated ECR-33, which is a partially rare earth (La) exchanged zeolite Q. In all of the above reports, the Si/Al ratio is 1.

Applicants have now synthesized a zeolite designated UZM-4, which appears to have a similar topology to that of zeolite Q, i.e., BPH, but has considerably different characteristics. The biggest difference is that UZM-4 has been synthesized with higher Si/Al ratios than zeolite Q, starting from a low of about 1.5 and going higher. The most important characteristic of UZM-4 is the greater thermal stability associated with the higher Si/Al ratios. UZM-4 in its various forms is stable to at least 400° C. and often up to greater than 600° C. The x-ray diffraction pattern of UZM-4 is noticeably different from that of zeolite-Q; and UZM-4 has smaller cell dimensions than that of zeolite Q, consistent with its higher Si/Al ratio.

SUMMARY OF THE INVENTION

As stated, the present invention relates to a new aluminosilicate zeolite designated UZM-4. Accordingly, one embodiment of the invention is a microporous crystalline zeolite having a three-dimensional framework of at least $AlO_2$ and $SiO_2$ tetrahedral units and an empirical composition on an as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from about 0.05 to about 0.95, R is at least one organic cation selected from the group consisting of protonated amines, protonated diamines, quaternary ammonium ions, diquaternary ammonium ions, protonated alkanolamines, and quaternized alkanolammonium ions, "r" is the mole ratio of R to (Al+E) and has a value of about 0.05 to about 0.95, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 0.5, "y" is the mole ratio of Si to (Al+E) and varies from about 1.5 to about 4 and "z" is the mole ratio of O to (Al+E) and has a value determined by the equation:

$$z=(m \cdot n+r \cdot p+3+4 \cdot y)/2$$

and is characterized in that it has the x-ray diffraction pattern having the d spacings and intensities set forth in Table A:

TABLE A

| 2–θ | d(Å) | I/I₀% |
|---|---|---|
| 6.45–6.75 | 13.69–13.08 | m |
| 7.52–7.80 | 11.75–11.33 | vs |
| 14.75–15.06 | 6.00–5.88 | w-m |
| 15.30–15.66 | 5.79–5.65 | w |
| 18.70–19.05 | 4.74–4.66 | w-m |
| 20.23–20.51 | 4.39–4.33 | w-m |
| 21.30–21.61 | 4.17–4.11 | m |
| 24.00–24.34 | 3.70–3.65 | m |
| 26.56–26.96 | 3.35–3.30 | w-m |
| 27.47–27.80 | 3.24–3.21 | w-m |
| 28.56–28.88 | 3.12–3.09 | w |
| 29.95–30.31 | 2.98–2.95 | m |
| 30.84–31.19 | 2.90–2.87 | w |
| 33.70–34.17 | 2.66–2.62 | w |
| 35.45–35.92 | 2.53–2.50 | w |
| 43.46–44.00 | 2.08–2.06 | w | and is thermally stable up to a temperature of about 400° C.

Another embodiment of the invention is a process for preparing the crystalline microporous zeolite described above. The process comprises forming a reaction mixture containing reactive sources of M, R, Al, Si and optionally E at a temperature of about 85° C. to about 225° C., the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.05 to about 1.5, "b" has a value of about 1.0 to about 15, "c" has a value of 0 to about 0.5, "d" has a value of about 2.5 to about 15, "e" has a value of about 25 to about 2500.

Yet another embodiment of the invention is a hydrocarbon conversion process using the above-described zeolite. The process comprises contacting the hydrocarbon with the zeolite at conversion conditions to give a hydroconverted hydrocarbon.

DETAILED DESCRIPTION OF THE INVENTION

Applicants have prepared an aluminosilicate zeolite and substituted versions of the same whose topological structure is related to BPH as described in *Atlas of Zeolite Structure Types*, W. H. Meier, D. H. Olson, and C.H. Baerlocher, editors, Elsevier, (1996), 68–69, which has been designated UZM-4. As will be shown in detail, UZM-4 is different from zeolite Q in a number of its characteristics. The instant microporous crystalline zeolite (UZM-4) has an empirical composition in the as-synthesized form and on an anhydrous basis expressed by the empirical formula:

$$M_m^{n+}R_r^{p+}Al_{1-x}E_xSi_yO_z$$

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. R is an organic cation and is selected from the group consisting of protonated amines, protonated diamines, quaternary ammonium ions, diquaternary ammonium ions, protonated alkanolamines and quaternized alkanolammonium ions. The value of "n" which is the weighted average valence of M varies from about 1 to about 2. The value of "p" which is the weighted average valence of R varies from 1 to about 2. The ratio of silicon to (Al+E) is represented by "y" which varies from about 1.5 to about 4.0. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of 0 to (Al+E) and is given by the equation $$z=(m \cdot n+r \cdot p+3+4 \cdot y)/2$$

Where M is only one metal, then the weighted average valence is the valence of that one metal, i.e. +1 or +2. However, when more than one M metal is present, the total amount of $$M_m^{n+}=M_{m1}^{(n1)+}+M_{m2}^{(n2)+}+M_{m3}^{(n3)+}+\ldots$$

and the weighted average valence "n" is given by the equation:

$$n = \frac{m_1 \cdot n_1 + m_2 \cdot n_2 + m_3 \cdot n_3 + \cdots}{m_1 + m_2 + m_3 \cdots}$$

Similarly when only one R organic cation is present, the weighted average valence is the valence of the single R cation, i.e., +1 or +2. When more than one R cation is present, the total amount of R is given by the equation.
ti $R_r^{p+}=R_{r1}^{(p1)+}+R_{r2}^{(p2)+}+R_{r3}^{(p3)+}$ and the weighted average valence "p" is given by the equation $$p = \frac{p_1 \cdot r_1 + p_2 \cdot r_2 + p_3 \cdot r_3 + \cdots}{r_1 + r_2 + r_3 + \cdots}$$

The microporous crystalline zeolite, UZM-4, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. When R is a quaternary ammonium cation or a quaternized alkanolammonium cation, the sources include the hydroxide, chloride, bromide, iodide and fluoride compounds. Specific examples include without limitation tetramethylammonium hydroxide, tetraethylammonium hydroxide, hexamethonium bromide, diethyldimethylammonium hydroxide, tetrapropylammonium hydroxide, tetramethylammonium chloride and choline chloride. R may also be introduced as an amine, diamine, or alkanolamine. Specific examples are N,N,N',N'-tetramethyl-1,6-hexanediamine, triethylamine, and triethanolamine.

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from about 0.05 to about 1.5, "b" varies from about 1.0 to about 15, "c" varies from about 0 to 0.5, "d" varies from about 2.5 to about 15, and "e" varies from about 25 to about 2500. If alkoxides are used, it is preferred to include a distillation or evaporative step to remove the alcohol hydrolysis products. The reaction mixture is now reacted at a temperature of about 85° C. to about 225° C. and preferably from about 125° C. to about 150° C. for a period of about 1 day to about 2 weeks and preferably for a time of about 2 days to about 4 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The UZM-4 aluminosilicate zeolite, which is obtained from the above-described process, is characterized by the x-ray diffraction pattern, having the d-spacings and relative intensities set forth in Table A below.

TABLE A

| 2–θ | d(Å) | I/I₀% |
|---|---|---|
| 6.45–6.75 | 13.69–13.08 | m |
| 7.52–7.80 | 11.75–11.33 | vs |
| 14.75–15.06 | 6.00–5.88 | w-m |
| 15.30–15.66 | 5.79–5.65 | w |
| 18.70–19.05 | 4.74–4.66 | w-m |
| 20.23–20.51 | 4.39–4.33 | w-m |

TABLE A-continued

| 2–θ | d(Å) | I/I$_o$% |
|---|---|---|
| 21.30–21.61 | 4.17–4.11 | m |
| 24.00–24.34 | 3.70–3.65 | m |
| 26.56–26.96 | 3.35–3.30 | w-m |
| 27.47–27.80 | 3.24–3.21 | w-m |
| 28.56–28.88 | 3.12–3.09 | w |
| 29.95–30.31 | 2.98–2.95 | m |
| 30.84–31.19 | 2.90–2.87 | w |
| 33.70–34.17 | 2.66–2.62 | w |
| 35.45–35.92 | 2.53–2.50 | w |
| 43.46–44.00 | 2.08–2.06 | w |

As will be shown in detail in the examples, the UZM-4 material is thermally stable up to a temperature of at least 400° C. and preferably up to about 600° C. The UZM-4 material has also been found to have a smaller unit cell size than zeolite Q, indicative of a higher Si/Al ratio. That is, a representative UZM-4 has a unit cell of a=13.269 Å, c=13.209 Å, versus a unit cell for zeolite Q of a=13.501 Å and c=13.403 Å.

As synthesized, the UZM-4 material will contain some of the exchangeable or charge balancing cations in its pores. These exchangeable cations can be exchanged for other cations, or in the case of organic cations, they can be removed by heating under controlled conditions. Because UZM-4 is a large pore zeolite, it is also possible to remove some organic cations directly by ion exchange.

The crystalline UZM-4 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-4 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. Nos. 4,310,440 and 4,440,871 which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204–649° C.), preferably between 600° and 950° F. (316–510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178–8,888 std. m$^3$/m$^3$), preferably between 2,000 and 30,000 scf per barrel of charge (355–5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-4 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic: olefin (e.g., benzene:olefin) ratio of between 5:1 and 30:1, a LHSV of about 0.3 to about 6 hr$^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. Nos. 5,157,196 and 5,157,197, which are incorporated by reference.

The following examples are presented in illustration of this invention and are not intended as undue limitations on the generally broad scope of the invention as set out in the appended claims.

The structure of the UZM-4 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100× I/I$_o$, the above designations are defined as $w=0–15; m=15–60; s=60–80$ and $vs=80–100$ In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLES

The following abbreviations will be used in the examples:

Al (Oi—Pr)$_3$ —aluminum isopropoxide
Al (Osec—Bu)$_3$ —aluminum sec—butoxide
DEDMAOH—diethyldimethylammonium hydroxide
HM —hexamethonium
TEAOH —tetraethylammonium hydroxide
TEOS —tetraethylorthosilicate
TMACl —tetramethylammonium chloride
TPAOH —tetrapropylammonium hydroxide

Example 1

An aluminosilicate reaction mixture was prepared having the following composition:

1.6 TEAOH: 1 TEOS: 0.52 Al(Osec—Bu)$_3$:35 H$_2$O. The reaction mixture was aged with stirring overnight at 85° C. and then distilled to 95° C. to remove solvent, forming a mixture containing 3.4% Si. Separately, a solution was prepared by dissolving 27.62 g tetramethylammonium chloride (97%) and 5.34 g LiCl in 50.0 g deionized water. This solution was added over a 5 minute period to 400.0 g of the above described aluminosilicate reaction mixture, using a high-speed mechanical stirrer. The resulting mixture was homogenized for 4 hr, placed in a 600 ml Parr Mini Stirred Reactor, ramped from room temperature to 150° C. over a period of 5 hr, held at 150° C. for 72 hr under autogenous pressure, and then cooled to room temperature. Solids were isolated by centrifugation, washed with deionized water, and dried at room temperature.

Elemental analysis revealed the material to have a Si/Al ratio of 1.85, Li/Al =0.46, and N/Al=0.32 giving (Li+N)/Al of 0.78. X-ray powder diffraction analysis showed that the product had the BPH topology. The d-spacings and relative intensities of the x-ray diffraction (XRD) are given in the Table 1 below. The product had a BET surface area of 483 m$^2$/g and was identified as UZM-4.

TABLE 1

| 2-θ | d(Å) | I/I$_0$ % |
|---|---|---|
| 6.66 | 13.16 | m |
| 7.72 | 11.44 | vs |
| 13.38 | 6.61 | m |
| 14.96 | 5.92 | w |
| 15.50 | 5.71 | w |
| 16.82 | 5.27 | w |
| 19.00 | 4.67 | m |
| 20.10 | 4.41 | w |
| 20.42 | 4.35 | m |
| 21.52 | 4.13 | m |
| 24.26 | 3.67 | m |
| 24.48 | 3.63 | w |
| 26.86 | 3.32 | m |
| 27.72 | 3.22 | m |
| 27.96 | 3.19 | w |

TABLE 1-continued

| 2-θ | d(Å) | I/I$_0$ % |
|---|---|---|
| 28.82 | 3.10 | w |
| 30.16 | 2.96 | m |
| 31.08 | 2.88 | w |
| 34.00 | 2.63 | w |
| 35.78 | 2.51 | w |
| 36.63 | 2.45 | w |
| 43.84 | 2.06 | w |

Example 2

An aluminosilicate reaction mixture was prepared having the following composition: 1.6 TEAOH: 1 TEOS: 0.5 Al(Osec—Bu)$_3$:35 H$_2$O. The reaction mixture was aged at 83° C. overnight and then distilled at 95° C. to remove solvents, forming a mixture containing 3.28% Si. Separately, a solution was prepared in which 1.33 g LiCl and 6.87 g TMACl (97%) were dissolved together in 15.0g deionized H$_2$O. This solution was added slowly to 103.1 g of the aluminosilicate reaction mixture described above. The reaction mixture was further homogenized for 3 hr, divided among 5 autoclaves and the mixtures were digested under a variety of conditions at autogenous pressures. The solids were isolated by centrifugation, washed with deionized water, and dried at room temperature.

Elemental analyses revealed that the product digested at 150° C. for 93 hr to have a Si/Al=1.96, N/Al=0.52, Li/Al= 0.38, and (N+Li)/Al=0.90. X-ray powder diffraction analysis showed that the product had the BPH topology. The d-spacings and relative intensities of the x-ray diffraction (XRD) are given in

TABLE 2

| 2-θ | d(Å) | I/I$_0$ % |
|---|---|---|
| 6.72 | 13.14 | m |
| 7.74 | 11.41 | vs |
| 13.42 | 6.59 | w |
| 15.02 | 5.89 | w |
| 15.56 | 5.69 | w |
| 16.58 | 5.25 | w |
| 19.00 | 4.67 | m |
| 20.44 | 4.34 | m |
| 21.56 | 4.12 | m |
| 24.28 | 3.66 | m |
| 26.86 | 3.32 | m |
| 27.74 | 3.21 | m |
| 28.82 | 3.10 | w |
| 30.22 | 2.96 | m |
| 31.06 | 2.88 | w |
| 34.08 | 2.63 | w |
| 35.80 | 2.51 | w |
| 43.84 | 2.06 | w |

Example 3

An aluminosilicate reaction mixture was prepared having the following composition: 1.2 TEAOH: 1 TEOS: 0.33 Al(Oi—Pr)$_3$: 35 H$_2$O. The reaction mixture was aged at 85° C. for 2 hr and then heated to 96° C. for 2.5 hr to remove solvents. The reaction mixture, which contained 3.54% Si, was allowed to cool. Separately, 38.53 g TMACl (97%) and 7.30 g LiOH*H$_2$O were dissolved together in 63.0 g deionized water. This solution was added slowly to 800.0 g of the aluminosilicate reaction mixture described above with vigorous mixing. The resultant mixture was further homogenized for 2 hr, divided among 6 autoclaves, and the mixtures were digested under a variety of conditions at autogenous pressures. The products were isolated by centrifugation, washed with deionized water, and dried at room temperature.

A sample digested for 6 days at 100° C. yielded a product with Si/Al=1.85, Li/Al=0.68, N/Al=0.41, and (N+Li)/Al= 1.09 by elemental analysis. Analysis by x-ray powder diffraction showed the material to have the BPH topology. Typical lines observed in the x-ray diffraction pattern are shown in Table 3. Analysis of the size and morphology of the crystallites by scanning electron microscopy (SEM) revealed mostly $0.1\mu$–$0.3\mu$ diameter hexagonal plates.

TABLE 3

| 2-θ | d(Å) | I/I$_0$ % |
| --- | --- | --- |
| 6.62 | 13.34 | m |
| 7.64 | 11.56 | vs |
| 13.32 | 6.64 | m |
| 14.88 | 5.95 | m |
| 15.40 | 5.75 | m |
| 16.72 | 5.30 | w |
| 18.90 | 4.69 | m |
| 20.10 | 4.41 | m |
| 20.32 | 4.37 | m |
| 21.42 | 4.14 | m |
| 24.14 | 3.68 | m |
| 26.78 | 3.33 | m |
| 27.62 | 3.23 | m |
| 28.76 | 3.10 | w |
| 30.08 | 2.97 | m |
| 30.96 | 2.89 | m |
| 33.94 | 2.64 | m |
| 35.63 | 2.52 | w |
| 36.53 | 2.46 | w |
| 43.70 | 2.07 | w |

Example 4

An aluminosilicate reaction mixture was prepared having the following composition: 1.6 TEAOH: 1 TEOS: 0.5 Al(Oi—Pr)$_3$: 35 H$_2$O. The reaction mixture was aged at 85° C. for 1 hr before it was heated to 96° C. to remove solvent. After solvent removal, the reaction mixture, which contained 3.53%Si, was allowed to cool. Separately, a solution was prepared in which 1.84 g LiCl and 16.24 g hexamethonium bromide were dissolved together in 20.00 g deionized water. This solution was added quickly to 138.0 g of the aluminosilicate reaction mixture described above, with vigorous stirring. The reaction mixture was homogenized for another hour before it was divided among 6 autoclaves, and the mixtures were digested under a variety of conditions at autogenous pressures. The products were isolated by centrifugation, washed with deionized water, and dried at room temperature.

The reactions in which the mixtures were digested at 150° C. and 175° C. for both 2 and 7 days all yielded products with the BPH topology as determined by x-ray powder diffraction. The product isolated from the 2 day —150° C. digestion had Si/Al=1.92, Li/Al=0.43, N/Al=0.46, and (N+Li)/Al=0.89. This sample was studied via variable temperature powder x-ray diffraction. The study was conducted with a flow of dry air over the sample. The BPH topology was observed to be stable to 600° C., the maximum temperature at which the study was conducted. A shift in some intensities of some of the lines was observed above the temperature where the organoammonium species decomposed. Table 4 gives the lines observed for the UZM-4 sample at room temperature and at 600° C. The results clearly establish the thermal stability of the UZM-4 composition.

TABLE 4

| Room Temperature, Li$_{0.43}$(HM)$_{0.23}$AlSi$_{1.92}$O$_{5.68}$ | | | 600° C., High Temperature XRD, Li$_{0.43}$(HM)$_{0.23}$AlSi$_{1.92}$O$_{5.68}$ | | |
| --- | --- | --- | --- | --- | --- |
| 2-θ | d(Å) | I/I$_0$ % | 2-θ | d(Å) | I/I$_0$ % |
| 6.48 | 13.63 | m | 6.84 | 12.91 | w |
| 7.60 | 11.62 | vs | 7.80 | 11.33 | vs |
| | | | 10.23 | 8.64 | w |
| 13.27 | 6.67 | w | 13.56 | 6.52 | w |
| 14.84 | 5.96 | w | 15.16 | 5.84 | m |
| 15.36 | 5.76 | w | 15.80 | 5.61 | w |
| 16.72 | 5.30 | w | | | |
| 18.84 | 4.71 | m | 19.24 | 4.61 | w |
| 20.32 | 4.37 | m | 20.57 | 4.32 | w |
| 21.44 | 4.14 | m | 21.76 | 4.08 | w |
| 24.16 | 3.68 | m | 24.80 | 3.59 | w |
| 26.80 | 3.32 | m | 27.08 | 3.29 | w |
| 27.64 | 3.23 | m | 27.93 | 3.19 | w |
| 28.68 | 3.11 | w | 29.08 | 3.07 | w |
| 30.12 | 2.96 | m | 30.60 | 2.92 | w |
| 31.04 | 2.88 | m | | | |
| 33.89 | 2.64 | w | 34.32 | 2.61 | w |
| 35.68 | 2.51 | w | | | |
| 43.80 | 2.07 | w | | | |

Example 5

An aluminosilicate reaction mixture was prepared having the following composition: 1.4 TEAOH: 1 TEOS: 0.4 Al(Osec—Bu)$_3$: 28 H$_2$O, employing vigorous stirring. The reaction mixture was aged at 75° C. overnight, heated to 85° C. for 3 hr to begin removing solvent, and finally held at 95° C. for 1 hr to complete the solvent removal process. This reaction mixture, which contained 3.57% Si, was allowed to cool to room temperature. Separately, two solutions were prepared by dissolving 68.78 g TMACl (97%) in 140 g H$_2$O and the second by dissolving 13.35 g LiCl in 30 g H$_2$O. To 1228 g of the aluminosilicate reaction mixture described above, the tetramethylammonium chloride solution was added with vigorous stirring. This was followed by the addition of the lithium chloride solution. The resulting reaction mixture was further homogenized for 4 hr. The majority of the reaction mixture, 1100 g, was placed in the teflon liner of a 2-liter autoclave and the mixture was digested quiescently at 140° C. for 3 days, while the rest of the reaction mixture was divided among 4–45 ml teflon-lined autoclaves. Two of these autoclaves were placed in a rotisserie oven, tumbled at 60 rpm and heated to a temperature of 150° C. for 2 and 4 days. The mixtures in the last two autoclaves were digested quiescently at 150° C. for 2 and 4 days. The solid products were isolated by centrifugation, washed with deionized water, and dried at room temperature.

The product isolated from the large quiescently digested sample had a Si/Al=2.34, Li/Al=0.49, N/Al=0.54, and (Li+N)/Al=1.03 as determined by elemental analyses. Analysis of the sample by powder x-ray diffraction showed the material to have the BPH topology, but there was a slight TMA-sodalite impurity. The lines observed in the x-ray diffraction pattern are given in Table 5. The samples digested in the 45 ml autoclaves, both quiescently and in the rotisserie oven, yielded products with the BPH topology only.

TABLE 5

| 2-θ | d(Å) | I/I₀ % | phase |
|---|---|---|---|
| 6.66 | 13.26 | m | BPH |
| 7.70 | 11.47 | vs | BPH |
| 13.30 | 6.65 | m | BPH |
| 13.96 | 6.34 | w | TMA SOD |
| 14.94 | 5.93 | w | BPH |
| 15.46 | 5.73 | w | BPH |
| 16.82 | 5.27 | w | BPH |
| 18.92 | 4.69 | m | BPH |
| 19.82 | 4.48 | w | TMA SOD |
| 20.36 | 4.36 | m | BPH |
| 21.52 | 4.13 | m | BPH |
| 24.24 | 3.67 | m | BPH/TMA SOD |
| 26.84 | 3.32 | w | BPH |
| 27.68 | 3.22 | m | BPH |
| 28.80 | 3.10 | w | BPH |
| 30.14 | 2.96 | m | BPH |
| 31.12 | 2.87 | w | BPH |
| 33.90 | 2.64 | w | BPH |
| 35.78 | 2.51 | w | BPH |
| 36.45 | 2.46 | w | BPH |
| 43.78 | 2.07 | w | BPH |

Example 6

An aluminosilicate reaction mixture was prepared by diluting 336.15 g TEAOH (35%) with 51.45 g $H_2O$, adding 52.04 g Al(Oi—Pr)3, (98%), and then 75.0 g Ludox# AS-40, with vigorous stirring over the course of the preparation. The reaction mixture was heated to 100° C. to remove some solvent before it was transferred to a teflon bottle and aged at 100° C. for 66 hr. The reaction mixture was allowed to cool to room temperature. A solution was prepared in which 34.26 g TMACl (97%) and 5.29 g LiCl were dissolved together in 35.0 g deionized water. This was added to the aluminosilicate reaction mixture in a single pour with vigorous stirring. The reaction mixture was homogenized for 2 hr before it was divided among 6 different autoclaves and digested under a variety of conditions at autogenous pressures. Solid products were isolated by centrifugation, washed with deionized water, and dried at room temperature.

The mixture digested at 125° C. for both 49 hr and 172 hr as well as the mixtures digested at 150° C. for 26 hr and 49 hr yielded materials with the BPH topology as determined by x-ray powder diffraction studies. Small amounts of amorphous material were also observed in the XRD as a shoulder on the baseline at low angle. The lines observed for the sample prepared at 125° C. for 49 hr are given in Table 6 below.

TABLE 6

| 2-θ | d(Å) | I/I₀ % |
|---|---|---|
| 6.46 | 13.67 | w |
| 7.56 | 11.68 | vs |
| 13.26 | 6.67 | w |
| 14.80 | 5.98 | w |
| 15.34 | 5.77 | w |
| 18.76 | 4.73 | w |
| 20.32 | 4.37 | w |
| 21.36 | 4.16 | m |
| 24.06 | 3.70 | m |
| 26.62 | 3.35 | w |
| 27.52 | 3.24 | w |
| 28.67 | 3.11 | w |
| 30.04 | 2.97 | m |
| 30.92 | 2.89 | w |

TABLE 6-continued

| 2-θ | d(Å) | I/I₀ % |
|---|---|---|
| 33.80 | 2.65 | w |
| 35.71 | 2.51 | w |
| 43.64 | 2.07 | w |

Example 7

An aluminosilicate reaction mixture was prepared with vigorous stirring having the following composition: 1 TEOS:0.5 Al(Osec—Bu)$_3$:0.8 TEAOH:12.5 $H_2O$. The reaction mixture was aged at 75° C. overnight, heated to 85° C. to remove some solvent, and then finally heated to 95° C. for an hour for complete removal of the solvent. The reaction mixture, which contained 7.5% Si, was recovered and cooled to room temperature. An 80.0 g portion of this reaction mixture was diluted with 20.0 g deionized water. Separately, 10.96 g TMACl (97%), 0.85 g LiCl, and 3.17 g Sr(NO$_3$)$_2$ were dissolved in 30.0 g deionized water. This solution was added to the diluted 100 g portion of the aluminosilicate reaction mixture described above with vigorous stirring. Once the addition was completed, the reaction mixture was homogenized for another 2 hr. The final reaction mixture was divided among 5 teflon-lined autoclaves, which mixtures were digested under a variety of conditions at autogenous pressures. The solid products were isolated by centrifugation, washed with deionized water, and dried at room temperature.

The samples digested at 150° C. for 2 and 3 days had the BPH topology, as determined by x-ray powder diffraction. A small amount of an unidentified impurity was also observed. This example shows that the BPH structure can be formed in a system containing much less organoammonium hydroxide than seen in the other examples above. A representative set of lines observed in the x-ray powder diffraction patterns of these samples is given in Table 7 below.

TABLE 7

| 2-θ | d(Å) | I/I₀ % | Phase |
|---|---|---|---|
| 6.60 | 13.38 | m | BPH |
| 7.68 | 11.50 | vs | BPH |
| 10.16 | 8.70 | w | BPH |
| 13.30 | 6.65 | m | BPH |
| 14.00 | 6.32 | w | Impurity |
| 14.86 | 5.96 | w | BPH |
| 15.48 | 5.72 | w | BPH |
| 16.02 | 5.53 | w | Impurity |
| 18.94 | 4.68 | m | BPH |
| 20.42 | 4.35 | m | BPH |
| 21.48 | 4.13 | m | BPH |
| 24.28 | 3.66 | m | BPH |
| 26.84 | 3.32 | m | BPH |
| 27.72 | 3.22 | w | BPH |
| 28.80 | 3.10 | m | BPH |
| 30.10 | 2.97 | m | BPH |
| 31.06 | 2.88 | w | BPH |
| 33.94 | 2.64 | m | BPH |
| 34.64 | 2.59 | w | BPH |
| 35.74 | 2.51 | w | BPH |
| 36.58 | 2.45 | w | BPH |
| 41.50 | 2.17 | w | BPH |
| 43.76 | 2.07 | w | BPH |

Example 8

An aluminosilicate reaction mixture was prepared having the following composition: 1 TEOS: 0.5 Al(Osec—Bu)$_3$: 1.6

TPAOH:35 H$_2$O. The reaction mixture was stirred overnight at 85° C. and was first distilled at 95° C. for one hour to remove solvent before continuing the distillation at 97° C. for an additional hour before allowing the reaction mixture to cool. A 300 g portion of this reaction mixture, which contained 2.88% Si, was placed in a teflon beaker and stirred with a high-speed mixer. Separately a solution was prepared by dissolving 18.76 g tetramethylammonium chloride (97%) and 3.52 g LiCl together in 20.0 g deionized water. This solution was added slowly to the aluminosilicate reaction mixture and homogenized for 4 hr. The homogenous reaction mixture was then divided among 6 teflon-lined autoclaves and the mixtures digested at autogenous pressures under a variety of temperatures and times. The solid products were isolated by centrifugation, washed with deionized water, and dried at room temperature.

Reaction mixtures digested at 125° C (2 and 4 days), 150° C (2 days), and 175° C. (2 days) yielded products with the BPH structure. A slight impurity was detected in the XRD in the form of a single peak at d=9.39Å. The patterns from all four of these samples were similar, representative lines for the material prepared at 175° C. are given in Table 8 below.

TABLE 8

| 2-θ | d(Å) | I/I$_0$ % | Phase |
| --- | --- | --- | --- |
| 6.64 | 13.29 | w | BPH |
| 7.68 | 11.50 | vs | BPH |
| 9.41 | 9.39 | w | Impurity |
| 13.28 | 6.66 | w | BPH |
| 14.88 | 5.95 | m | BPH |
| 15.52 | 5.71 | w | BPH |
| 16.78 | 5.28 | w | BPH |
| 18.90 | 4.70 | m | BPH |
| 20.09 | 4.42 | w | BPH |
| 20.38 | 4.35 | m | BPH |
| 21.48 | 4.13 | m | BPH |
| 24.24 | 3.67 | m | BPH |
| 24.36 | 3.65 | m | BPH |
| 26.80 | 3.32 | m | BPH |
| 27.68 | 3.22 | m | BPH |
| 27.92 | 3.19 | w | BPH |
| 28.80 | 3.10 | w | BPH |
| 30.12 | 2.96 | m | BPH |
| 31.04 | 2.88 | w | BPH |
| 33.92 | 2.64 | w | BPH |
| 34.12 | 2.63 | w | BPH |
| 35.76 | 2.51 | w | BPH |
| 36.66 | 2.45 | w | BPH |
| 43.78 | 2.07 | w | BPH |

Example 9

An aluminosilicate reaction mixture was prepared having the following composition: 1 TEOS:0.5 Al(Osec—Bu)$_3$: 1.6 TPAOH:35 H$_2$O. The reaction mixture was stirred overnight at 85° C. and was first distilled at 95° C. for one hour to remove solvent before continuing the distillation at 97° C. for an additional hour before allowing the reaction mixture to cool. A 200 g portion of this reaction mixture, which contained 2.88% Si, was placed in a teflon beaker and stirred with a high-speed mixer. Separately a solution was prepared by dissolving 20.62 g hexamethonium bromide and 2.34 g LiCl together in 25.0 g deionized water. This solution was added slowly to the aluminosilicate reaction mixture and homogenized for 4 hr. The homogenous reaction mixture was then divided among 4 teflon-lined autoclaves, and the mixtures were digested at autogenous pressures at a variety of temperatures and times. The solid products were isolated by centrifugation, washed with deionized water, and dried at room temperature.

Reaction mixtures digested at 150° C. (7 days), 175° C. (2 and 4 days), and 200° C. (2 days) yielded products with the BPH structure. The patterns from all four of these samples were similar; representative lines for the material prepared at 200° C. are given in Table 9 below.

TABLE 9

| 2-θ | d(Å) | I/I$_0$ % |
| --- | --- | --- |
| 6.58 | 13.42 | w |
| 7.74 | 11.41 | vs |
| 13.42 | 6.59 | w |
| 14.96 | 5.92 | w |
| 15.62 | 5.67 | w |
| 16.75 | 5.29 | w |
| 18.98 | 4.67 | w |
| 19.86 | 4.47 | w |
| 20.46 | 4.34 | m |
| 21.56 | 4.12 | m |
| 24.18 | 3.68 | m |
| 26.90 | 3.31 | w |
| 27.74 | 3.21 | w |
| 28.82 | 3.10 | w |
| 30.24 | 2.95 | m |
| 31.08 | 2.88 | w |
| 33.96 | 2.64 | w |
| 35.82 | 2.50 | w |
| 43.90 | 2.06 | w |

Example 10

An aluminosilicate reaction mixture was prepared having the following composition: 1 SiO$_2$:0.25 Al$_2$O$_3$:1 TEAOH:20 H$_2$O. To 253.6 g of a solution of aluminum chlorhydrol (23% Al$_2$O$_3$), there were added 268 g of NH$_4$OH (29% NH$_3$) with stirring. The resulting alumina precipitate was isolated by filtration, washed with about 3 L deionized water, and then transferred to a beaker containing 962.5 g TEAOH (35%). Once the alumina had been added, 343.2 g of Ludox™ AS-40 was added to the reaction mixture. After homogenizing for an hour, the reaction mixture was aged in a teflon bottle for 2 days at 100° C. After the aging period, the reaction mixture was allowed to cool and was transferred to another bottle for storage. This reaction mixture contained 4.17% Si and 1.90% Al and is designated Mixture A. A portion of Mixture A, 150 g, was treated with 56.22 g TEAOH (35%) and vigorously homogenized for 30 minutes. Separately, an additional solution was prepared by dissolving 11.89 g TMACl (97%) and 2.24 g LiCl together in 13.0 g deionized water. This latter solution was then added dropwise to the aluminosilicate reaction mixture and homogenized further for 4 hr. The reaction mixture was then split among 4 different autoclaves and the mixtures were digested under a variety of conditions at autogenous pressures. The solid products were isolated by centrifugation, washed with deionized water and dried at room temperature.

Two of the mixtures were digested for 52 hrs, one at 125° C. and the other at 150° C. The sample digested at 125° C. was in a rotisserie oven, which was tumbled at 60 rpm. Analysis by x-ray powder diffraction showed that the products from both of these reactions had the BPH topology. Representative lines for the product isolated from the 125° C. reaction is shown in Table 10 below.

TABLE 10

| 2-θ | d(Å) | I/I$_0$ % |
| --- | --- | --- |
| 6.67 | 13.24 | m |
| 7.68 | 11.50 | vs |
| 13.37 | 6.62 | m |
| 14.90 | 5.94 | m |
| 15.46 | 5.73 | w |

TABLE 10-continued

| 2-θ | d(Å) | I/I₀ % |
|---|---|---|
| 16.79 | 5.28 | w |
| 18.94 | 4.68 | m |
| 20.17 | 4.40 | w |
| 20.39 | 4.35 | m |
| 21.48 | 4.13 | m |
| 24.22 | 3.67 | m |
| 24.47 | 3.63 | w |
| 26.82 | 3.32 | m |
| 27.67 | 3.22 | m |
| 27.88 | 3.20 | w |
| 28.77 | 3.10 | w |
| 30.16 | 2.96 | m |
| 31.05 | 2.88 | w |
| 33.92 | 2.64 | w |
| 35.71 | 2.51 | w |
| 36.63 | 2.45 | w |
| 37.46 | 2.40 | w |
| 38.38 | 2.34 | w |
| 39.11 | 2.30 | w |
| 39.84 | 2.26 | w |
| 40.69 | 2.22 | w |
| 41.40 | 2.18 | w |
| 43.75 | 2.07 | w |
| 44.23 | 2.05 | w |
| 47.35 | 1.92 | w |
| 49.48 | 1.84 | w |
| 50.15 | 1.82 | w |

Example 11

An aluminogallosilicate UZM-4 was prepared as follows. A gallosilicate reaction mixture was prepared by diluting 245.90 g TEAOH (35%) with 146.45 g deionized water, adding 86.66 g Ludox™ AS-40 and finally 116 g of freshly precipitated Ga(OH)₃. The reaction mixture was vigorously stirred for 1 hr and then aged at 95° C. in a teflon bottle for a day. After aging, the reaction mixture, which will be designated Mixture B, contained 2.81% Si and 2.38% Ga. An aluminosilicate reaction mixture, Mixture A described in Example 10, 87.29 g, was placed in a teflon beaker equipped with a high-speed stirrer. With vigorous stirring, 45.02 g of Mixture B was added. This was followed by the addition of 49.59 g TEAOH (35%) and homogenization for an hour. Separately a solution was prepared by dissolving 1.63 g LiCl and 8.68 g TMACl (97%) in 5.3 g deionized water. This solution was added to the aluminogallosilicate reaction mixture after the initial hour of homogenization. The reaction mixture was further homogenized for 2 hours before it was divided among 6 teflon-lined autoclaves and the mixtures were digested under a variety of conditions at autogenous pressures. The products were isolated by centrifugation, washed with deionized water, and dried at 100° C.

All of the products contained BPH species, but those that were formed under the mild conditions of 125° C. for either 2 or 4 days showed only BPH topology in their x-ray diffraction patterns. Representative lines in the x-ray diffraction pattern are given in Table 11. Elemental analysis of the sample gave Si/(Al+Ga)=1.77, Ga/(Al+Ga)=0.048, for the framework elements and Li/(Al+Ga)=0.64, N/(Al+Ga)=0.50 and (Li+N)/(Ga+Al)=1.14 for the cation balance.

TABLE 11

| 2-θ | d(Å) | I/I₀ % |
|---|---|---|
| 6.58 | 13.42 | m |
| 7.62 | 11.60 | vs |
| 13.26 | 6.67 | m |
| 14.82 | 5.97 | m |
| 15.34 | 5.77 | m |
| 16.68 | 5.31 | w |
| 18.82 | 4.71 | m |
| 20.06 | 4.42 | m |
| 20.28 | 4.38 | m |
| 21.36 | 4.16 | m |
| 24.12 | 3.69 | m |
| 26.70 | 3.34 | m |
| 27.52 | 3.24 | m |
| 27.86 | 3.20 | m |
| 28.62 | 3.12 | w |
| 30.02 | 2.97 | s |
| 30.92 | 2.89 | m |
| 33.80 | 2.65 | m |
| 35.56 | 2.52 | w |
| 36.46 | 2.46 | w |
| 39.04 | 2.31 | w |
| 40.50 | 2.23 | w |
| 41.34 | 2.18 | w |
| 43.56 | 2.08 | m |

Example 12

An aluminosilicate reaction mixture was prepared by the addition of 38.76 g aluminum hydroxide (52.5% Al₂O₃) to 1428.6 g DEDMAOH (20%) with vigorous stirring. Colloidal silica (Ludox™ AS-40), 300 g was then added to the stirring mixture, which was homogenized further for 4 hr. The mixture was then placed in a teflon bottle and digested overnight at 100° C. Elemental analysis showed the mixture to contain 3.26% Si. This aluminosilicate mixture is designated Mixture C and will be used in another example. A portion of Mixture C, 100 g, was placed in a teflon beaker equipped with a high-speed stirrer. Separately, 0.5 g LiCl was dissolved in 3 g deionized water. This solution was added to the aluminosilicate reaction mixture with vigorous stirring. After 3 hr of homogenization, the reaction mixture was split among several teflon-lined autoclaves, which were sealed, placed in ovens and digested at autogenous pressures. The products were isolated by centrifugation, washed with deionized water, and dried at 100° C.

The product resulting from a digestion at 100° C. for 6 days exhibited a powder x-ray diffraction pattern consistent with the BPH topology of UZM-4. Elemental analysis showed the product to have Si/Al=2.21, Li/Al=0.43, N/Al=0.41 and for the cation balance (Li+N)/Al=0.84. Characteristic lines of this product are given in Table 12.

TABLE 12

| 2-θ | d(Å) | I/I₀ % |
|---|---|---|
| 6.60 | 13.38 | m |
| 7.64 | 11.57 | vs |
| 10.12 | 8.74 | w |
| 13.30 | 6.65 | m |
| 14.88 | 5.95 | w |
| 15.38 | 5.76 | m |
| 16.74 | 5.29 | w |
| 18.90 | 4.69 | m |
| 20.10 | 4.41 | m |
| 20.36 | 4.36 | m |
| 21.46 | 4.14 | s |
| 24.16 | 3.68 | s |

TABLE 12-continued

| 2-θ | d(Å) | I/I₀ % |
|---|---|---|
| 24.44 | 3.64 | m |
| 26.82 | 3.32 | m |
| 27.64 | 3.22 | m |
| 28.74 | 3.10 | m |
| 30.12 | 2.96 | s |
| 31.04 | 2.88 | m |
| 33.92 | 2.64 | m |
| 35.72 | 2.51 | w |
| 36.58 | 2.45 | w |
| 37.31 | 2.41 | w |
| 38.40 | 2.34 | w |
| 39.18 | 2.30 | w |
| 39.84 | 2.26 | w |
| 40.72 | 2.21 | w |
| 41.40 | 2.18 | m |
| 43.74 | 2.07 | m |
| 44.38 | 2.04 | w |
| 47.36 | 1.92 | w |
| 49.54 | 1.84 | w |
| 50.16 | 1.82 | m |

Example 13

The aluminosilicate reaction mixture designated as Mixture C in example 12 was used as a source of Si and Al in this example. Mixture C, 100 g, was placed in a teflon beaker equipped with a stirrer. To the stirring mixture 2.68 g TMACl (97%) was added. Separately, 0.5 g LiCl was dissolved in 2.0 g deionized water. The reaction mixture was allowed to stir for several hours. After homogenization, the reaction mixture was divided among 4 teflon-lined autoclaves, which were digested under a variety of reaction conditions at autogenous pressures. The products were isolated by centrifugation, washed with deionized water, and dried at 95° C.

All of the products contained UZM-4 as determined by powder x-ray diffraction. A sample digested for 6 days at 125° C. was well-crystallized; characteristic x-ray lines for the product are shown in Table 13. Elemental analysis of this product revealed an Si/Al ratio of 2.53.

TABLE 13

| 2-θ | d(Å) | I/I₀ % |
|---|---|---|
| 6.64 | 13.30 | m |
| 7.60 | 11.62 | vs |
| 13.28 | 6.66 | m |
| 14.86 | 5.96 | w |
| 15.42 | 5.74 | w |
| 16.76 | 5.29 | w |
| 18.88 | 4.70 | m |
| 20.38 | 4.35 | s |
| 21.44 | 4.14 | m |
| 24.20 | 3.67 | m |
| 26.78 | 3.33 | m |
| 27.64 | 3.22 | m |
| 28.80 | 3.10 | w |
| 30.12 | 2.96 | m |
| 31.04 | 2.88 | m |
| 33.98 | 2.64 | m |
| 35.72 | 2.51 | w |
| 36.64 | 2.45 | w |
| 40.72 | 2.21 | w |
| 41.40 | 2.18 | w |
| 43.74 | 2.07 | m |

Example 14

U.S. Pat. No. 2,991,151 discloses that zeolite Q is synthesized using potassium as the charge balancing ion. As a comparison, the process used in the previous examples was carried out using potassium as the charge-balancing ion. An aluminosilicate reaction mixture was prepared by combining 1 TEOS: 0.5 Al(Osec—Bu)₃: 1.6 TEAOH:41.5 H₂O, employing vigorous stirring. The resulting mixture was placed in a teflon bottle and aged for 3 days in a 100° C. oven. The reaction mixture, which contained about 2.93% Si, was then allowed to cool to room temperature. A portion of this reaction mixture, 130.0 g, was placed in a teflon beaker and agitated with a high speed stirrer. A potassium chloride solution, prepared by dissolving 10.15 g KCl in 30.0 g H₂O, was added to the aluminosilicate reaction mixture slowly with vigorous stirring. The resulting mixture was homogenized for a half hour before it was divided among 7 teflon-lined autoclaves, which mixtures were digested under a variety of conditions at autogenous pressures. The digestion conditions employed were typical for the formation of the BPH topology aluminosilicates disclosed in the examples given above. The solid products were isolated by centrifugation, washed with deionized water, and dried at room temperature.

The mixtures in three of the autoclaves were digested at 150° C. for 2, 6, and 10 days. A fourth autoclave was digested at 100° C. for 6 days. All of these conditions yielded well-crystallized products with the MER topology, there was no sign of material with the BPH topology. Representative lines from the x-ray powder diffraction pattern are shown in Table 14 below.

TABLE 14

| 2-θ | d(Å) | I/I₀ % | Phase |
|---|---|---|---|
| 8.83 | 10.00 | w | MER |
| 10.84 | 8.16 | m | MER |
| 12.50 | 7.07 | s | MER |
| 16.59 | 5.34 | m | MER |
| 17.76 | 4.99 | s | MER |
| 19.87 | 4.47 | m | MER |
| 20.36 | 4.36 | w | MER |
| 20.85 | 4.26 | m | MER |
| 21.80 | 4.07 | w | MER |
| 22.89 | 3.88 | w | impurity |
| 24.41 | 3.64 | w | MER |
| 26.01 | 3.42 | w | impurity |
| 27.56 | 3.23 | vs | MER |
| 28.26 | 3.16 | vs | MER |
| 30.38 | 2.94 | m | MER |
| 32.93 | 2.72 | m | MER |
| 33.56 | 2.67 | m | MER |
| 35.37 | 2.54 | m | MER |
| 37.12 | 2.42 | w | MER |
| 38.24 | 2.35 | w | MER |

Example 15

The UZM-4 material prepared in example 5 was tested for ion exchange using the following procedure. About 10–12 g of the zeolite was treated with a chloride or nitrate solution of the exchanging cation. The pH of the cation exchange solution was adjusted to the range of 7–8 by using KOH or LiOH. The resulting slurry was heated to 75° C. with stirring for 1–2 hr before the product was isolated by filtration and washed. This procedure was carried out 5–6 times. Data is presented for the compositions of the parent zeolite, the exchanged zeolite, the calcined exchanged zeolite, and the structure of the exchanged material after calcination. Table 15 shows the compositions as determined by elemental analyses, where cation deficiencies with respect to the charge balance on the zeolite are assumed to be accounted for by $H^+$, which is included in the formulations below even though it was not directly determined by the analyses. It should be pointed out in the examples below the ease with which the organic cations are exchanged from these UZM-4 materials. This is consistent with the large 12-ring pore system known for the BPH topology.

TABLE 15

| Exchange Cation | Composition Exchanged Zeolite | Composition Calcined Exchanged Zeolite/Calcination Temp | Structure of Calcined Exchanged Zeolite |
|---|---|---|---|
| | Parent Zeolite: Example 5, $Li_{0.49}(NR_4)_{0.54}AlSi_{2.34}O_{6.69}$ | | |
| $NH_4^+$ | $N_{0.83}Li_{0.03}AlSi_{2.36}O_{6.72}$ | $H_{0.97}Li_{0.03}AlSi_{2.36}O_{6.72}/500°$ C. | Amorphous |
| $K^+$ | $K_{0.84}Li_{0.04}(NR_4)_{0.08}AlSi_{2.31}O_{6.62}$ | $H_{0.06}K_{0.84}Li_{0.04}N_{0.06}AlSi_{2.31}O_{6.62}/350°$ C. | BPH |
| | Parent Zeolite: $Li_{0.49}(NR_4)_{0.50}AlSi_{2.17}O_{6.34}$ | | |
| $Ca^{2+}$ | $Ca_{0.46}Li_{0.04}(NR_4)_{0.06}AlSi_{2.15}O_{6.32}$ | $H_{0.07}Ca_{0.44}Li_{0.05}AlSi_{2.13}O_{6.23}/430°$ C. | BPH |
| $La^{3+}$ | $La_{0.28}Li_{0.15}(NR_4)_{0.14}AlSi_{2.17}O_{6.41}$ | $H_{0.11}Li_{0.14}La_{0.25}AlSi_{2.14}O_{6.28}/430°$ C. | BPH |
| $Li^+$ | $(NR_4)_{0.13}Li_{0.94}AlSi_{2.18}O_{6.40}$ | $H_{0.05}Li_{0.95}AlSi_{2.16}O_{6.32}/430°$ C. | BPH |

Example 16

UZM-4 was analyzed by $^{29}Si$ and $^{27}Al$ NMR and is compared to the NMR spectrum of zeolite Q in the literature. Zeolite Q has been studied by Andries, Bosmans, and Grobert, in *Zeoltes*, vol. 11, p.116–131 (1991). The zeolite Q sample with Si/Al=1 showed in the $^{29}Si$ nmr spectrum, three lines with chemical shifts that were consistent with 4 Al in the Si environment. The narrow linewidths observed for these lines indicated that there was Si and Al ordering in the framework. In contrast, $^{29}Si$ nmr spectra of a typical higher Si/Al BPH topology UZM-4 sample showed five broad lines (each line is actually multiple lines), corresponding to Si in a variety of environments, differing by the number of aluminums (0–4) in the immediate coordination sphere of Si. This broader distribution of coordination environments is expected for materials with an excess of Si over Al, see G. Engelhardt, D. Michel, *High Resolution Solid State NMR of Silicates and Zeolites*, 1987, John Wiley and Sons, p. 134–157. $^{27}Al$ nmr showed that all the Al is tetrahedral in the UZM-4 material. This is also the case for zeolite Q reported by Andries. The $^{29}Si$ and $^{27}Al$ chemical shifts are given for zeolite Q and the higher silica UZM-4 samples in Table 15 below, along with possible interpretations, see G. Engelhardt, D. Michel, *High Resolution Solid State NMR of Silicates and Zeolites*, 1987, John Wiley and Sons, p. 134–157. The differences between the UZM-4 and zeolite Q are quite apparent.

TABLE 16

| Sample | Chemical shift (ppm)/interpretation |
|---|---|
| Zeolite Q, $^{29}Si$ nmr (Andries et al.) | $-84.8, -86.0, -89.9/Q^4(4Al)$ |
| Zeolite Q, $^{27}Al$ nmr (Andries et al.) | 61.2/tetrahedral Al |
| UZM-4, $^{29}Si$ nmr (this work) | $-84.8 \ Q^4(4Al); -89.7 \ Q^4(3Al), Q^4(4Al);$ $-93.6/Q^4(2Al); -100.0/Q^4(1Al); -104.8/Q^4(0Al)$ |
| UZM-4, $^{27}Al$ nmr (this work) | 57.1/tetrahedral Al |

We claim as our invention:

1. A microporous crystalline zeolite having a three dimensional framework of at least $AlO_2$ and $SiO_2$ tetrahedral units and an empirical composition on an as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from about 0.05 to about 0.95, R is at least one organic cation selected from the group consisting of protonated amines, quaternary ammonium ions, diquaternary ammonium ions, protonated alkanolamines and quaternized alkanolammonium ions, "r" is the mole ratio of R to (Al+E) and has a value of about 0.05 to about 0.95, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from about 0 to about 0.5, "y" is the mole ratio of Si to Al and varies from about 1.5 to about 4.0 and "z" is the mole ratio of O to Al and has a value determined by the equation:

$$z=(m \cdot n+r \cdot p+3+4 \cdot y)/2$$

and is characterized in that it has the x-ray diffraction pattern having the d spacings and intensities set forth in Table A:

TABLE A

| 2-θ | d(Å) | $I/I_0\%$ |
|---|---|---|
| 6.45–6.75 | 13.69–13.08 | m |
| 7.52–7.80 | 11.75–11.33 | vs |
| 14.75–15.06 | 6.00–5.88 | w-m |
| 15.30–15.66 | 5.79–5.65 | w |
| 18.70–19.05 | 4.74–4.66 | w-m |
| 20.23–20.51 | 4.39–4.33 | w-m |
| 21.30–21.61 | 4.17–4.11 | m |
| 24.00–24.34 | 3.70–3.65 | m |
| 26.56–26.96 | 3.35–3.30 | w-m |
| 27.47–27.80 | 3.24–3.21 | w-m |
| 28.56–28.88 | 3.12–3.09 | w |
| 29.95–30.31 | 2.98–2.95 | m |
| 30.84–31.19 | 2.90–2.87 | w |
| 33.70–34.17 | 2.66–2.62 | w |
| 35.45–35.92 | 2.53–2.50 | w |
| 43.46–44.00 | 2.08–2.06 | w | and is thermally stable up to a temperature of about 400° C.

2. The zeolite of claim 1 where said zeolite is thermally stable up to a temperature of about 600° C.

3. The zeolite of claim 1 where M is selected from the group consisting of lithium, sodium, cesium, strontium, barium and mixtures thereof and R is a quaternary ammonium ion.

4. The zeolite of claim 3 where the quaternary ammonium ion is selected from the group consisting of tetramethylammonium, tetraethylammonium, hexamethonium, diethyldimethylammonium, tetrapropylammonium and mixtures thereof.

5. The zeolite of claim 1 where M is a mixture of an alkali metal and an alkaline earth metal and R is a quaternary ammonium ion.

6. The zeolite of laim 1 where R is a quaternized alkanolamine.

7. The zeolite of claim 6 where the quaternized alkanolamine is choline or methyltriethanolammonium.

8. A process for preparing a microporous crystalline zeolite having a three dimensional framework of at least $AlO_2$ and $SiO_2$ tetrahedral units and an empirical composition on an as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from about 0.05 to about 0.95, R is at least one organic cation selected from the group consisting of protonated amines, quaternary ammonium ions, diquaternary ammonium ions, protonated alkanolamines and quaternized alkanolammonium ions, "r" is the mole ratio of R to (Al+E) and has a value of about 0.05 to about 0.95, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from about 0 to about 0.5, "y" is the mole ratio of Si to Al and varies from about 1.5 to about 4.0; the process comprising forming a reaction mixture containing reactive sources of M, R, Al, Si and optionally E at a temperature of about 85° C. to about 225° C., the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.05 to about 1.5, "b" has a value of about 1.0 to about 15, "c" has a value of 0 to about 0.5, "d" has a value of about 2.5 to about 15, "e" has a value of about 25 to about 2500, wherein the zeolite is characterized in that it has the x-ray diffraction pattern having the d-spacings and intensities set forth in Table A:

TABLE A

| 2–θ | d(Å) | I/I$_0$% |
|---|---|---|
| 6.45–6.75 | 13.69–13.08 | m |
| 7.52–7.80 | 11.75–11.33 | vs |
| 14.75–15.06 | 6.00–5.88 | w-m |
| 15.30–15.66 | 5.79–5.65 | w |
| 18.70–19.05 | 4.74–4.66 | w-m |
| 20.23–20.51 | 4.39–4.33 | w-m |
| 21.30–21.61 | 4.17–4.11 | m |
| 24.00–24.34 | 3.70–3.65 | m |
| 26.56–26.96 | 3.35–3.30 | w-m |
| 27.47–27.80 | 3.24–3.21 | w-m |
| 28.56–28.88 | 3.12–3.09 | w |
| 29.95–30.31 | 2.98–2.95 | m |
| 30.84–31.19 | 2.90–2.87 | w |
| 33.70–34.17 | 2.66–2.62 | w |
| 35.45–35.92 | 2.53–2.50 | w |
| 43.46–44.00 | 2.08–2.06 | w |

9. The process of claim 8 where M is selected from the group consisting of lithium, sodium, cesium, strontium, barium and mixtures thereof and R is a quaternary ammonium ion.

10. The process of claim 8 where the source of M is selected from the group consisting of halide, nitrate, sulfate, hydroxide, or acetate salts.

11. The process of claim 9 where R is a quaternary ammonium cation selected from the group consisting of tetramethylammonium, tetraethylammonium, hexamethonium, diethyldimethylammonium, tetrapropylammonium and mixtures thereof.

12. The process of claim 9 where the source of R is the halide or hydroxide compounds of R.

13. The process of claim 9 where the aluminum sources are selected from the group consisting of aluminum isopropoxide, aluminum sec-butoxide, precipitated alumina and aluminum metal.

14. The process of claim 9 where the silicon sources are selected from the group consisting of tetraethylorthosilicate, colloidal silica, fumed silica and precipitated silica.

15. The process of claim 9 where the E sources are selected from the group consisting of alkali borates, boric acid, gallium oxyhydroxide, gallium sulfate, ferric sulfate, ferric chloride, chromium nitrate, indium chloride and mixtures thereof.

16. A hydrocarbon conversion process comprising contacting the hydrocarbon with a catalytic composite at hydrocarbon conversion conditions to give a converted product, the catalytic composite comprising a microporous crystalline zeolite having a three dimensional framework of at least $AlO_2$ and $SiO_2$ tetrahedral units and an empirical composition on an as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from about 0.05 to about 0.95, R is at least one organic cation selected from the group consisting of protonated amines, quaternary ammonium ions, diquaternary ammonium ions, protonated alkanolamines, and quaternized alkanolammonium ions, "r" is the mole ratio of R to (Al+E) and has a value of about 0.05 to about 0.95, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from about 0 to about 0.5, "y" is the mole ratio of Si to Al and varies from about 1.5 to about 4.0 and "z" is the mole ratio of O to Al and has a value determined by the equation:

$$z=(m \cdot n+r \cdot p+3+4 \cdot y)/2$$

and is characterized in that it has the x-ray diffraction pattern having the d spacings and intensities set forth in Table A:

TABLE A

| 2–θ | d(Å) | I/I$_0$% |
|---|---|---|
| 6.45–6.75 | 13.69–13.08 | m |
| 7.52–7.80 | 11.75–11.33 | vs |
| 14.75–15.06 | 6.00–5.88 | w-m |
| 15.30–15.66 | 5.79–5.65 | w |
| 18.70–19.05 | 4.74–4.66 | w-m |
| 20.23–20.51 | 4.39–4.33 | w-m |
| 21.30–21.61 | 4.17–4.11 | m |
| 24.00–24.34 | 3.70–3.65 | m |

TABLE A-continued

| 2–θ | d(Å) | I/I₀% |
|---|---|---|
| 26.56–26.96 | 3.35–3.30 | w-m |
| 27.47–27.80 | 3.24–3.21 | w-m |
| 28.56–28.88 | 3.12–3.09 | w |
| 29.95–30.31 | 2.98–2.95 | m |
| 30.84–31.19 | 2.90–2.87 | w |
| 33.70–34.17 | 2.66–2.62 | w |
| 35.45–35.92 | 2.53–2.50 | w |
| 43.46–44.00 | 2.08–2.06 | w | and is thermally stable up to a temperature of about 400° C.

* * * * *